United States Patent [19]

McCarthy

[11] Patent Number: 5,558,102
[45] Date of Patent: Sep. 24, 1996

[54] UNIVERSAL TIE-LESS PATIENT LIMB RESTRAINT DEVICE

[76] Inventor: Andrew D. McCarthy, 5507 Albia Rd., Bethesda, Md. 20816

[21] Appl. No.: 257,279

[22] Filed: Jun. 9, 1994

Related U.S. Application Data

[63] Continuation-in-part of Ser. No. 723,049, Jun. 28, 1991, Pat. No. 5,161,545, and a continuation-in-part of Ser. No. 973,974, Nov. 9, 1993, abandoned.

[51] Int. Cl.$^6$ .................................................. A61F 5/37
[52] U.S. Cl. ........................................ 128/878; 128/876
[58] Field of Search ........................... 128/869, 876–882, 128/846, 874

[56] References Cited

U.S. PATENT DOCUMENTS

| | | | |
|---|---|---|---|
| 2,606,554 | 8/1952 | Simon | 128/881 |
| 2,706,477 | 4/1955 | Daake | 128/878 X |
| 3,027,895 | 4/1962 | Williams | 128/878 |
| 4,414,969 | 11/1983 | Heyman | 128/878 |
| 4,628,925 | 12/1986 | Witzel | 128/878 |
| 4,832,053 | 5/1989 | McCarthy | 128/878 |
| 5,016,650 | 5/1991 | Marlor | 128/878 |
| 5,161,545 | 11/1992 | McCarthy | 128/869 |

*Primary Examiner*—Robert A. Hafer
*Assistant Examiner*—Brian E. Hanlon
*Attorney, Agent, or Firm*—A. R. Eglington

[57] ABSTRACT

A limb restraint device is for ready assembly/detachment with a patient, and while in use, for remote anchoring to limit exaggerated limb flexing. It includes a flexible fabric member of rectangular configuration having a ribbon-like member presenting a closed circle which is secured to one short end and so secured as to provide two hemispherical loops for engaging a tethering strap. Complemental adhering members are provided adjacent to each transverse end and are adapted to interruptably engage each other when a patient limb is enclosed. An elongate anchoring strap is operably connected to the loops serving to reinforce the fabric member enclosure and concurrently tether the limb to a remote anchoring post.

5 Claims, 6 Drawing Sheets

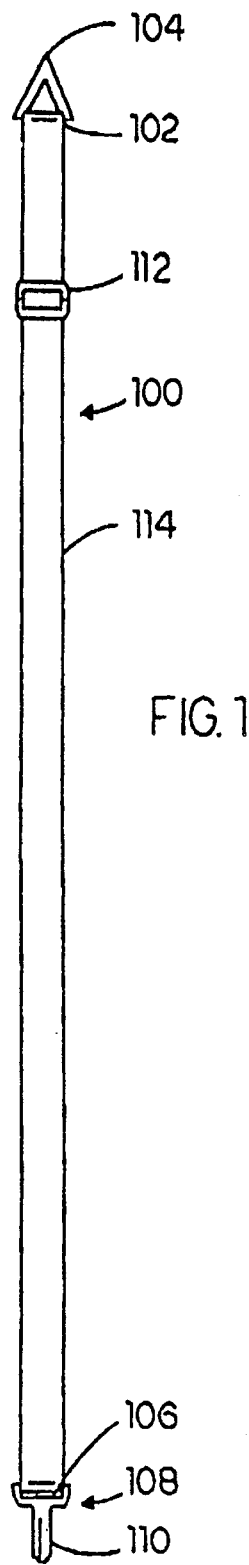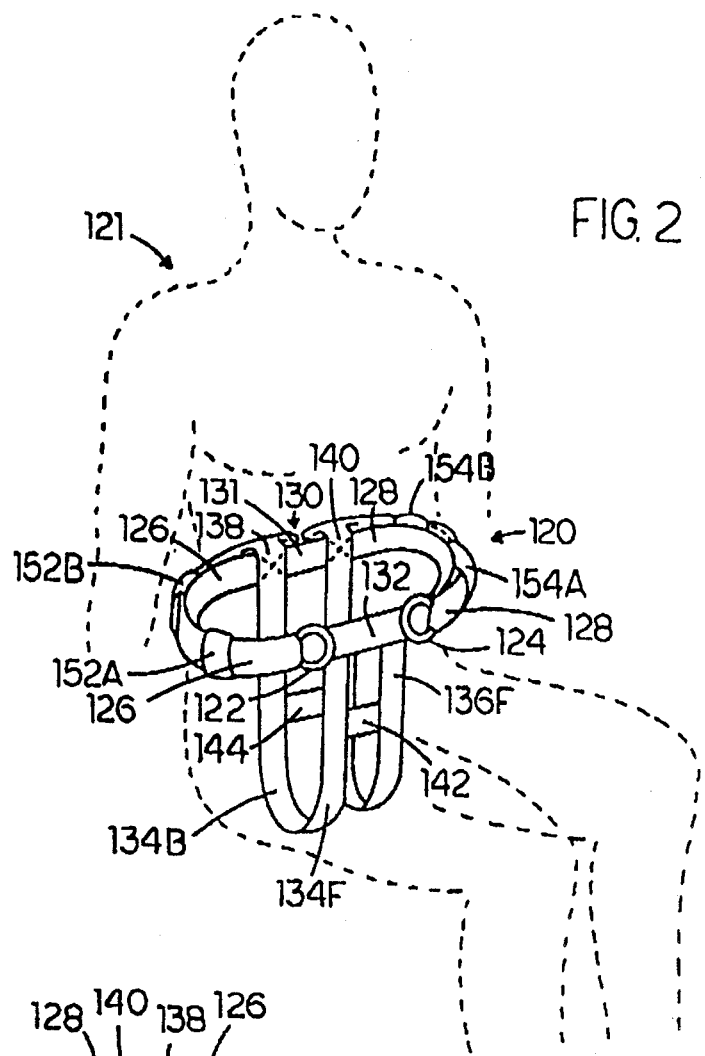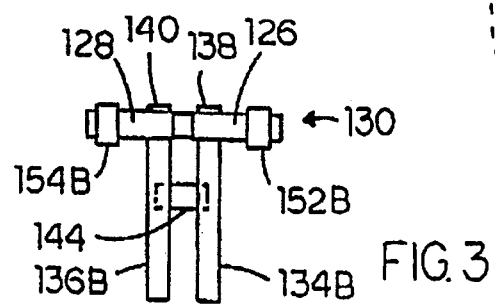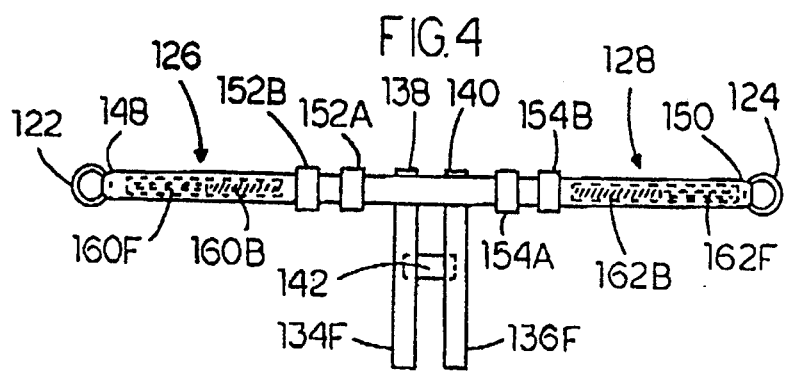

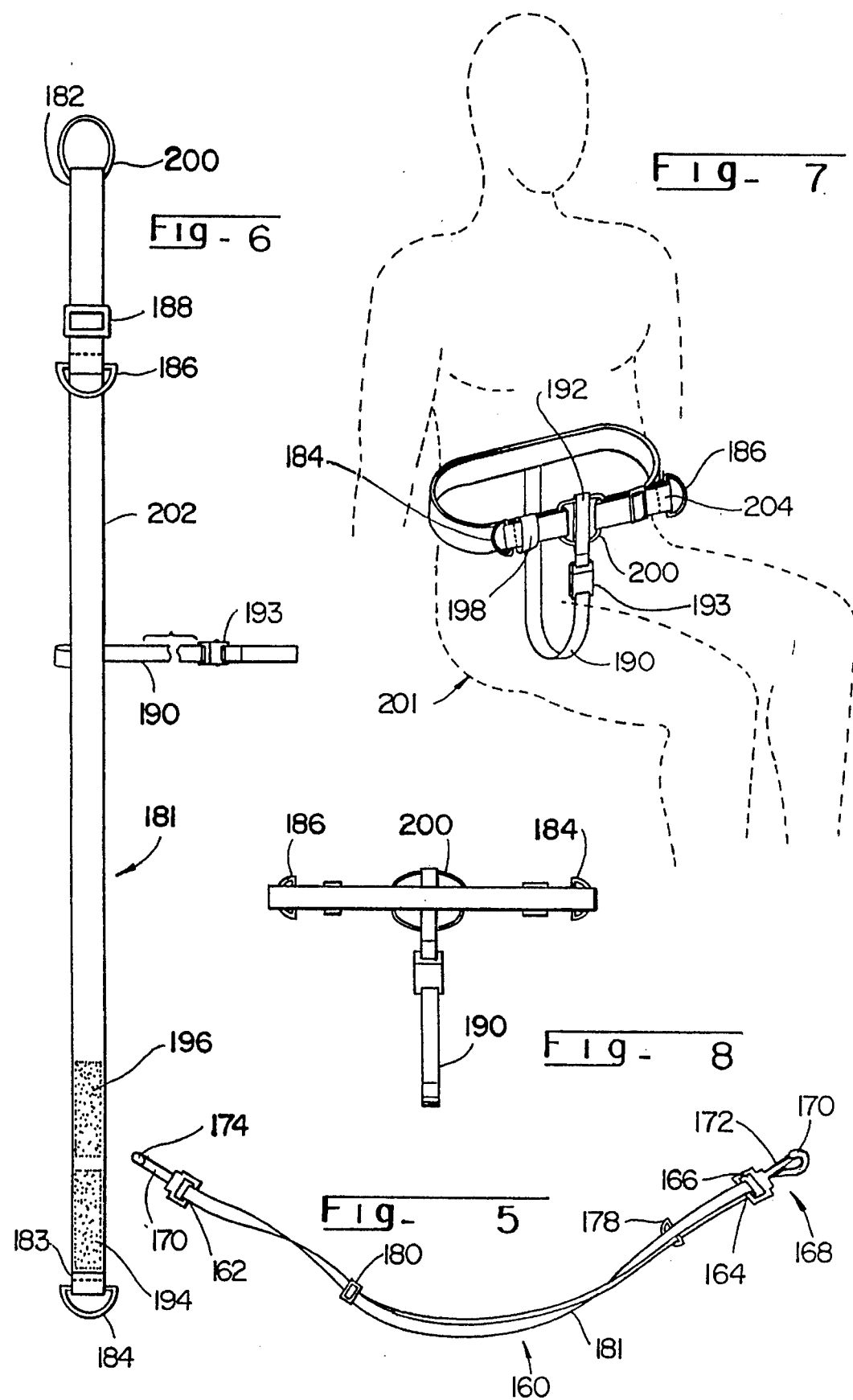

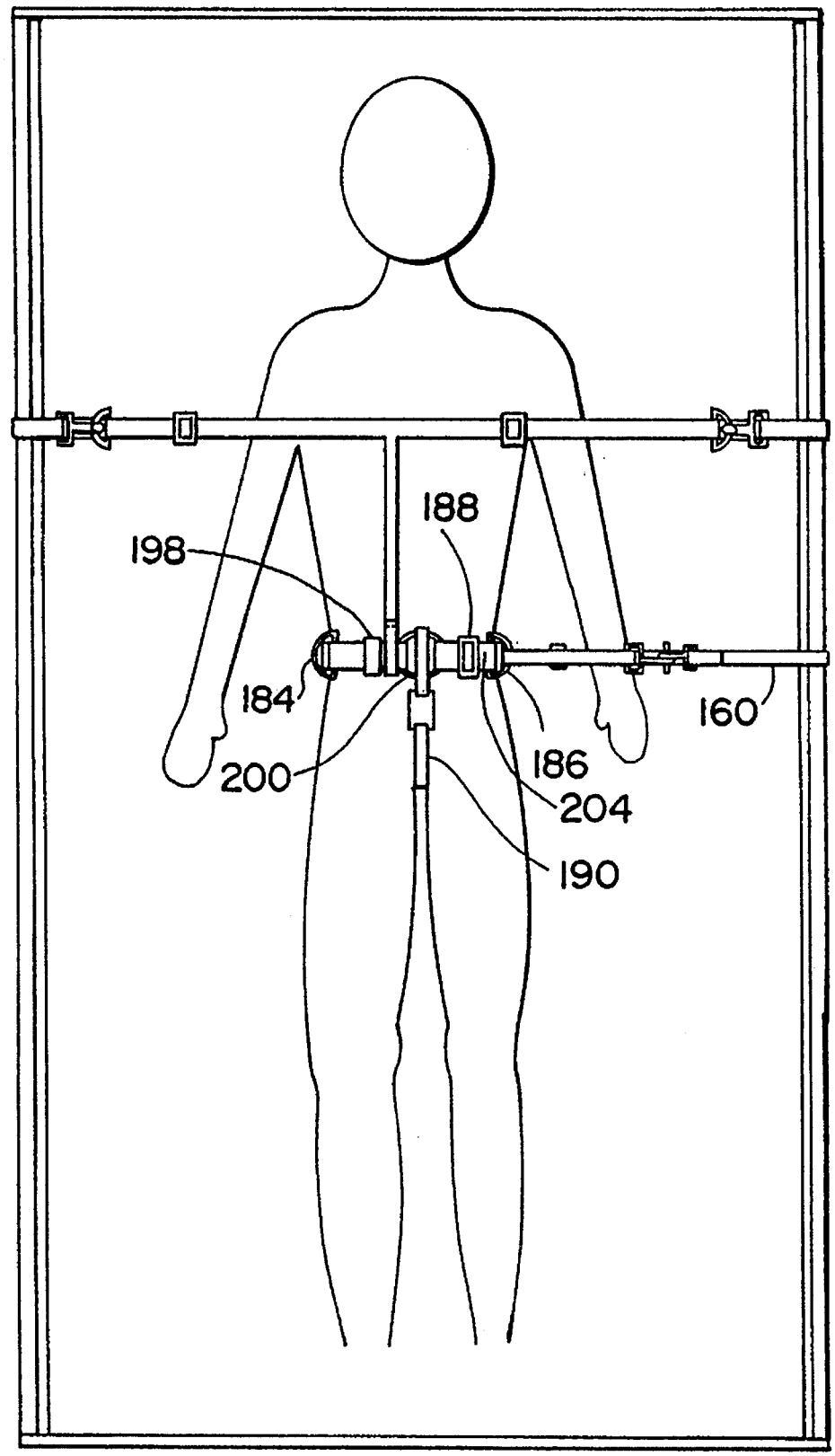
Fig_ 9

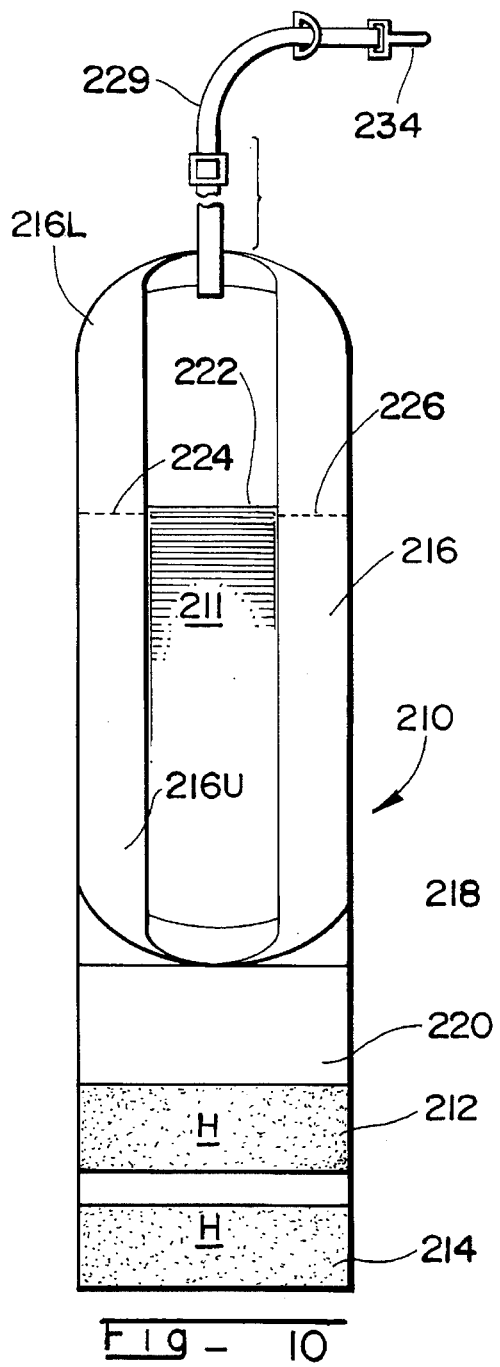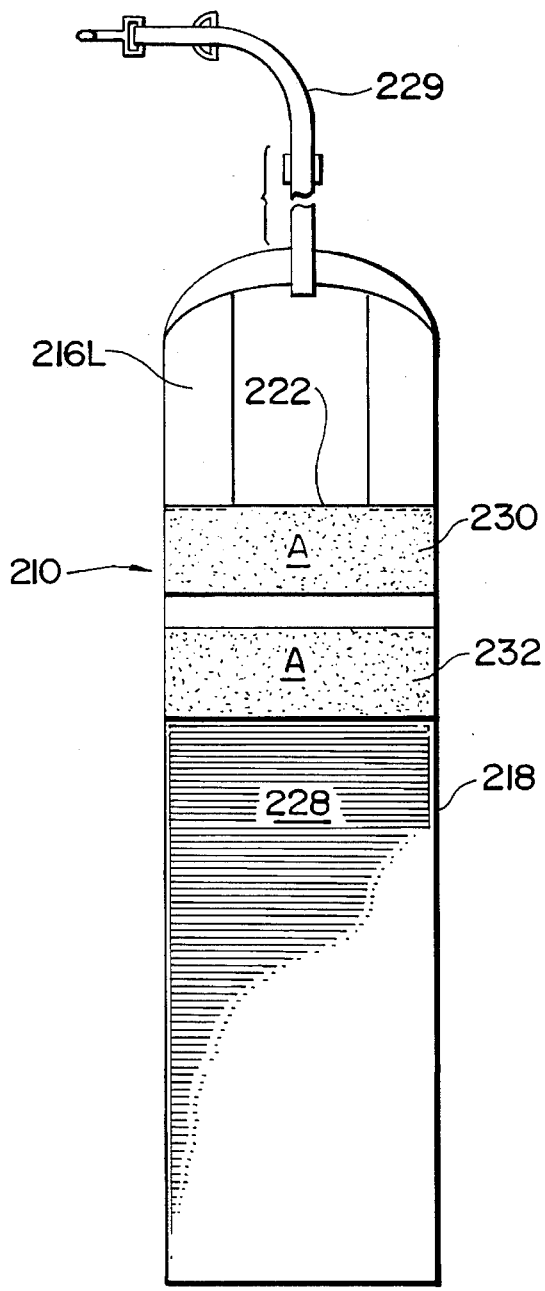

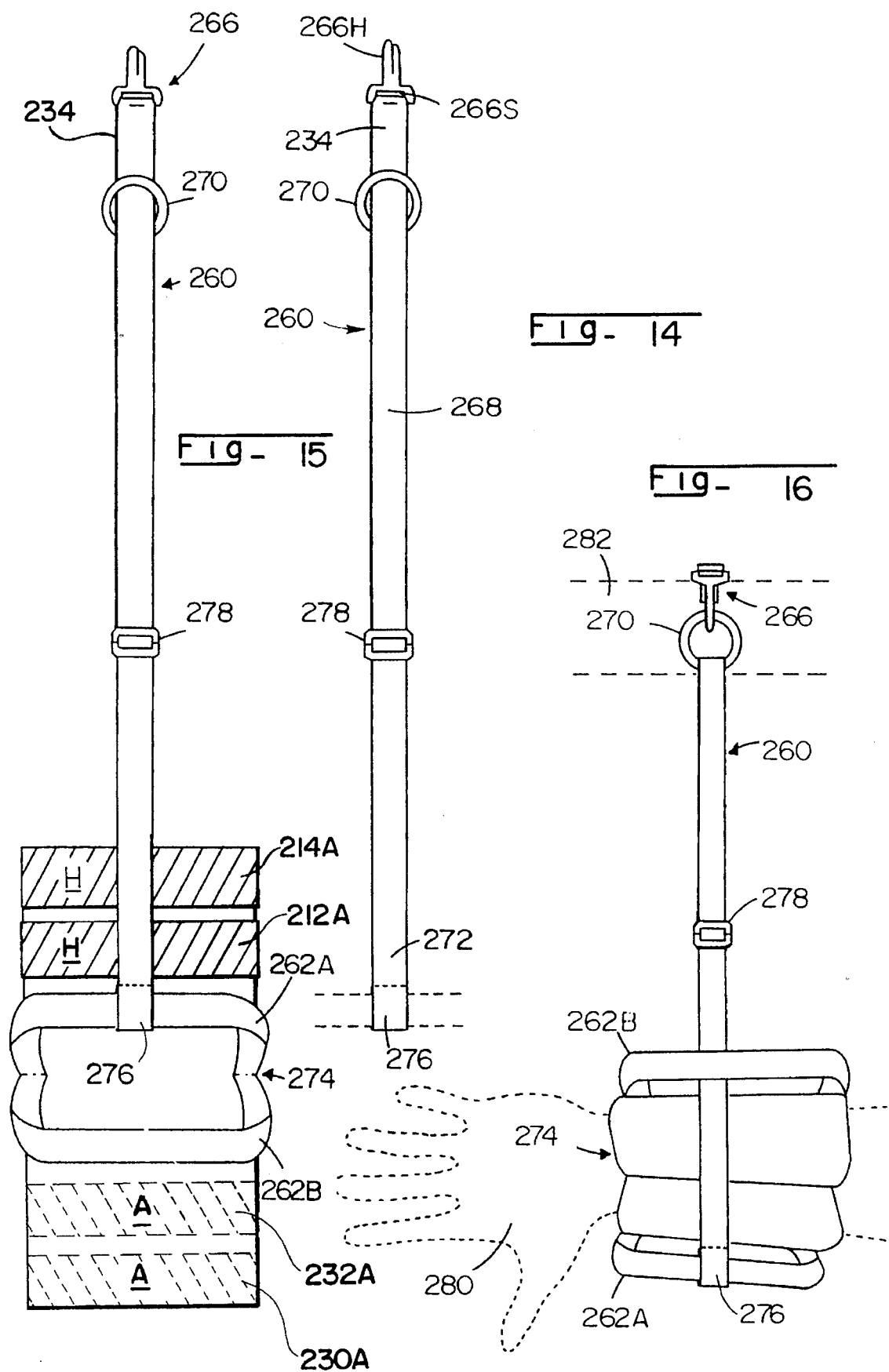

UNIVERSAL TIE-LESS PATIENT LIMB RESTRAINT DEVICE

This application is a continuation-in-part of, my application Ser. No. 07/723,049, filed Jun. 28, 1991, now U.S. Pat. No. 5,161,545 and also of my application Ser. No. 07/973,974, filed Nov. 9, 1993 now abandoned.

The present invention relates to a limb restraint device including a padded flexible member, an attached cloth means forming dual symmetrical loops and aligned pairs of complemental hooks-locking segments located on the opposing planar surface at the opposing ends of the fabric member. A separable anchoring strap engages slidingly with the symmetrical loops, providing overall controlled play of the limb.

The present invention also discloses safety belts for a chair-bound patient to preclude slipping down and out of the chair. The unique belt is cooperatively associated with the safety vest proper.

BACKGROUND OF THE INVENTION

A wide range of patients must be protected against unsafe and unhealthful movement—principally falling out of body supports such as a bed, tables and chairs, or by moving their body portions, and thereby rupturing sutures, or otherwise causing further injury to already impaired body portions. Without being secured in such supports by health care personnel, such patients are likely to cause serious injury to themselves. Such patients include comparative invalids, as well as those who have sufficient consciousness and strength to attempt to disengage such restraints; or to engage in substantial movement, but who are also subject to sufficient aggression, disorientation, or other debilitating condition, that disengaging their own restraints would likely result in injury to them. However, since the subject being restrained is a patient who is suffering from a medical disability, such restraint must be comfortable and not overly confining in use to be acceptable.

In sum, despite their long history of use, and the variety of forms offered, serious mishaps do occur to agitated patients, even when currently available vest or limb restraints are employed.

A safety belt for the lower torso serves to control waist movement in a secure manner. Available waist restraints basically use straps to control movement but are not really secure; thus often tend to work upwardly and regrettably may even act as a strangulation ligature. A restraint device is needed that precludes any upward belt slippage but is still adaptable to ready release from a patient torso for personal hygiene needs and other manage care purposes.

In the area of limb restraints, in addition to the first embodiment disclosed and claimed in my copending parent U.S. Ser. No. 07/723,049, mow U.S. Pat. No. 5,161,545, alternate embodiments may require only an integral anchor strap and a somewhat simplified form of padding for gaining adequate wrist application.

It is a principal object of this invention to provide a limb restraint device adapted to limit excess limb flexing including padded flexible fabric member and cloth adapted for double looping and cooperation with an adjustable anchoring means of the prior art.

A still further object of the invention is to provide a belt-like harness for the lower patient torso, which cooperates with my U.S. Pat. No. 4,832,053 vest restraint, and so precludes a vested patient, who is also a chair-bound, from wriggling down and out of the supporting chair even while his upper torso is adequately vested.

Other objects and advantages of the present invention will become apparent from the following specification and from the drawings and the claims.

SUMMARY OF THE INVENTION

According to the invention, in a first aspect there is provided; a safety harness for enclosing the lower torso of a seated patient comprising an elongate flexible fabric belt having a central segment and two pairs of strap loop means mounted spaced apart on the central segment; a closely adjacent pair of elongate complemental adhering means mounted on one side of the central segment, the paired adhering segments being located intermediate the looping means on the free end of the elongate strap free end; a ring-like closure member secured to each strap free end; a depending pair of fabric restraining straps, being each secured at one longitudinal end to the belt front side and being of sufficient length to comfortably encircle the lower patient torso; and a pair of flexible cross members, each attached proximal to the free ends of the opposing restraining straps, and thereby limit the strap tendency to diverge unduly when mounted about the patient's buttocks.

In the other major aspect of the invention, there is provided a wrist restraint device suited for readily interruptable contact with a human wrist comprising a first flexible fabric member having a central padding section of a generally rectangular planar configuration, a flexible cloth, ribbon-like means presenting a closed loop which is fastened diametrically to the opposing linear margins of the fabric member, thus presenting two hemispherical loops, one of which is adapted for sliding engagement with a torso strap; a first pair of complemental adhesive pile and/or hook-locking segments mounted on one planar surface proximal to one longitudinal end of the fabric member, also being spaced apart from the padded segment; a second pair of complemental pile and/or hook-locking segments similarly mounted on the opposing surface being proximal to the other longitudinal end of the fabric member;

The complemental adhering segments of both pairs are arrayed so as to overlap and have the first adhering pair make secure contact with the opposing second pair of adhering segments; and while the slidingly engaged anchoring strap is being adapted to pass sequentially through each of the hemi-loops then having its free end terminate in a strap attachment and release means; such a tethering strap being of sufficient adjustable length to be looped around a support post, which post is usually spaced well apart from the limb (wrist) restraint itself.

In another embodiment of the limb restraint device, the engagable elements of the anchoring strap comprise a permanent loop provided at the one longitudinal end of the anchoring strap, that is normally engaged with one of said hemispherical loops, also a ring-like closure means freely tracking the strap length along the transverse strap width, and a manually-activated hooking means disposed at the other strap longitudinal end.

In another embodiment of the restraint device the flexible fabric member is also provided with an integral padded segment proximal its mid-section, which adapted to provide a cushioning effect upon the restraint assembly and during the cinching of the anchor strap about the restraint device and also during its concurrent tethering to a remote post for patient protection.

In another embodiment of the restraint device the adhering segments are located proximal to each longitudinal end of the fabric member, on opposing planar surfaces thereof, each segment comprises a pair of complemental adhering pile and hook-locking segments, configured so as to make contact when the one end is disposed to overlap the other end, whereby the hook-locking pad segment on the one end will make adhering contact with the pile pad segment on the other end.

In another useful embodiment of the device, the adhering segment on the first fabric surface comprises a substantially parallel, spaced-apart pair of such adhering pile segments, and further wherein the adhering segment on the second fabric surface comprises a substantially parallel, spaced-apart pair of complemental hook-locking segments, which will make interruptable contact with the opposing pile segments.

BRIEF DESCRIPTION OF THE INVENTION FIGURES

FIG. 1 is a plan view of one anchoring strap component of the invention, functionally identical to the anchoring strap depicted in FIG. 4 of my U.S. Pat. No. 4,832,053, but modified only slightly as to one of the terminal mating elements at its longitudinal end as to ring configuration, with such anchoring strap being securable to remote stationary posts in a ready manner, (see FIG. 2, 3, and 4, next to be described);

FIG. 2 is a perspective view of the chest side of a first embodiment of safety belt adapted for a patient's lower torso useful in cooperation with the safety vest described in the afore tested U.S. Pat. No. '053, and showing a restrained (partial) patient torso in phantom;

FIG. 3 is an elevational view of the reverse side of the safety belt of FIG. 2, as it protectively engages a seated patient's lower rear torso, and also depicts an offset pair of spaced-apart, vertical harnesses which embrace the patient's buttocks;

FIG. 4 is an elevational view of the safety belt device (stomach side) but with the extending out of the now unfastened free ends, so to depict the underlying complemental set of fastener segments, located on each of the respective extended fastener straps, which engage securely during the free end looping back, leaving the ring-like, longitudinal ends adapted for anchor strap coupling;

FIG. 5 is a perspective view of another embodiment of an anchoring strap component of the invention, modified to be operatively associated with the safety belt of FIG. 7;

FIG. 6 is a top plan view of one external surface of the second embodiment of the safety belt, especially adapted to cooperate with a second embodiment of the anchoring strap, and depicting the pile and hook-locking segments located only on one longitudinal end of that surface, and the intermediately appended crotch strap with its attachable free end;

FIG. 7 is a perspective view from the stomach side of this second embodiment of the safety belt serving to restrain a patient's lower torso;

FIG. 8 is an elevational view of the rearward side of the safety belt of FIG. 7, as it would appear while it protectively engages a seated patient's lower rear torso (no phantom), and also depicts the single vertical strap encircling the patient's buttocks;

FIG. 9 is a top plan view of a bed-ridden patient utilizing the lower torso restraint device of FIG. 6, which is cooperatively engaged with an upper torso, T-shaped, transverse restraining strap;

Figure 12:
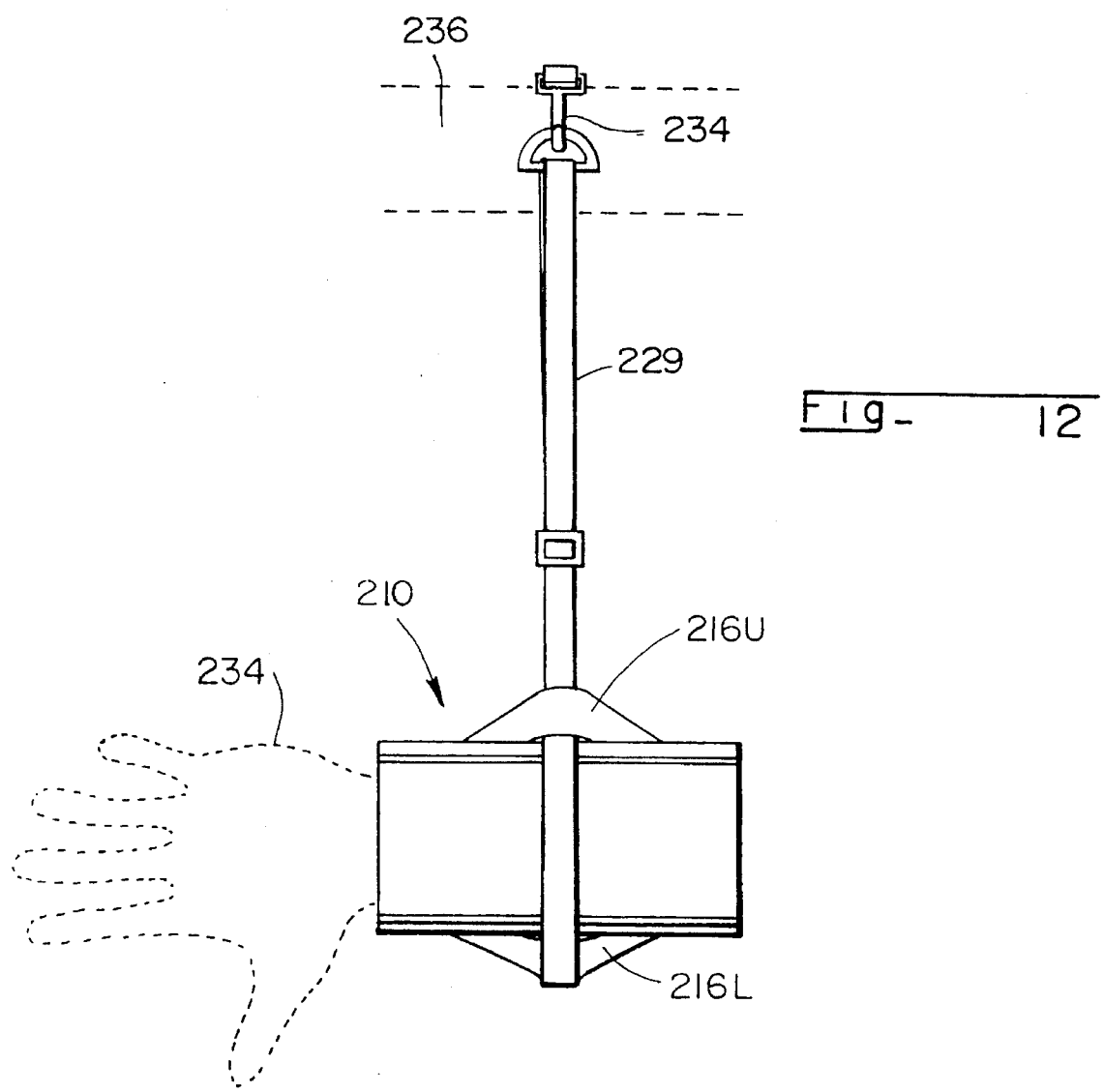
Figure 13:
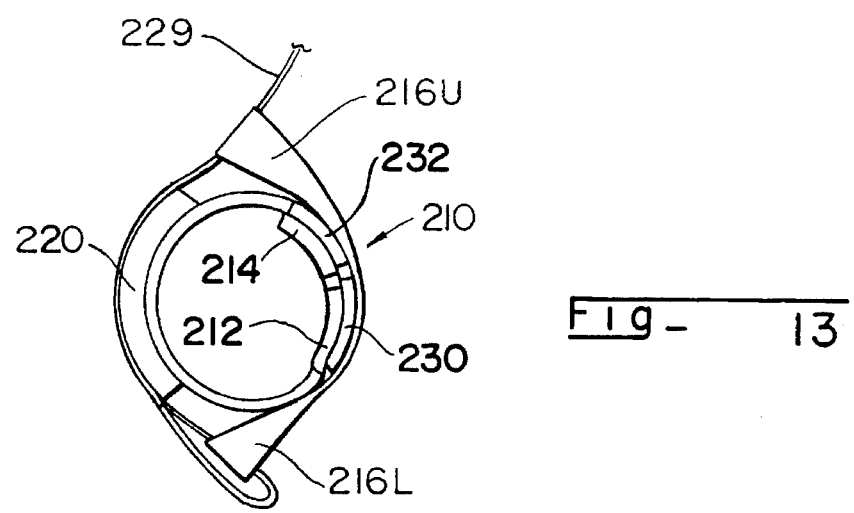

FIG. 10 is an elevational view of one surface of a safety device limb restraint which is particularly adapted for patient wrist restraint, depicting a centrally mounted dual padded section, one free end-mounted, two-loop securing means; at the other end, the mounting of a set of complemental transverse, pad-like fastening means, and an operatively associated anchoring strap adapted for remote hitching;

FIG. 11 is an elevational view of the opposing planar surface of the device of FIG. 10 depicting a second set of complemental fastening pads (hook/pile) which are end-mounted at the other longitudinal end and adjacent the two-loop;

FIG. 12 is a perspective view of the wrist restraint device of FIGS. 10/11, while its ends are folded into use by cradling of a patient's forearm, also with an anchoring strap now threaded longitudinally through the other fabric loop, as well, and thereafter extending to a remote post (not seen);

FIG. 13 is a vertical end view taken axially of the folded strap depicting the intervening position of a central foam pad located between the encircled limb and loop-cinched and tautly extended anchor strap.

FIG. 14 is a plan view of an alternate embodiment of an anchoring strap, especially adapted for cooperating with the patient wrist restraint device of FIG. 15, usable in place of the standard anchoring strap 100 of FIG. 1;

FIG. 15 is a top elevational view of the anchor strap of FIG. 14 now functionally [entwined] linked with another embodiment to a limb restraint device, but prior to actual limit engagement; and FIG. 16 is a perspective view of the anchor strap of FIG. 14, functionally entwined and cooperating usefully with a human wrist being restrained by the limb restraint of FIG. 15, thereby depicting how restrained limbs can be safely tethered to a support chair or post or in which a patient has been seated.

DETAILED DESCRIPTION OF THE PREFERRED EMBODIMENT

In FIG. 1, is a top plan view of the anchoring strap component 100, laid out in its full extension, as it would appear before its use in the present invention. At its one longitudinal end 102, the anchor strap terminates in a rigid, conveniently triangular attachment means, such as a metal (or formed plastic) ring 104. This ring can be secured similarly to rings 27, 28, employed on the free ends of the fastener straps 16, 17 of FIG. 1 of my U.S. Pat. No. 4,832,053.

The other longitudinal end of anchor strap 100 is looped through a transversely configured, rigid slot 106 of fastener 108. Slot 106 is integral with the conventional snap spring fastener 108, typically one with a partial hook-shaped rigid end and a cooperating flexible metal (or plastic) snap strip 110. Snap 110 is biased to be normally closed within the inner tip (not seen) of the hooked end. Strip 110 is adapted to be manually depressed so as to permit instant release of any ensnared ring, like closure means 104 of FIG. 1.

Ring means 104 of anchor strap 100 (FIG. 1) is the one with which the other complemental snappable joinder means 108 will cooperate, after the anchoring strap 100 is properly looped through a safety vest fastener strap rings. The elongate free fabric portion of anchor strap 100, which is located intermediate ring 104 and snap fastener 110 (not seen), is held by a conventional double-slot, rigid buckle 112. The slidable buckle 112 tracks itself along on the free fabric length 114 of the anchor strap 100 proper. In this manner, the overall length of anchor strap 100 is substantially variable, but is also still a presetable one, so as to tightly straddle the distance between the vest attachment point (its fastener rings), and the particular type of remote stationary post(s), to be employed with the vest while in use, usually bed railings.

As for the juxtapositions of the Velcro fastener, as to its complemental components, the adhesive pile component may be more conveniently mounted proximal to the tied ends of the fastening straps, while the multiple hook pads are mounted proximal to the free ends of the fastener straps. Either arrangement is operable, but that just described is preferred for ease of manipulation of fastening straps.

TORSO RESTRAINT DEVICE

An ancillary device that can be usefully employed with the just described safety vest is the belt restraint means of FIGS. 2 to 4. In the perspective view of FIG. 2, such a safety belt 120 is depicted, as it would appear mounted on the lower torso of a seated patient 121, who may also be wearing a safety vest, as well. If so, the free ringed ends 122, 124 of dual horizontal belting straps 126 and 128 of belt 120 would be threaded through the lower loops 33C and 33D on the prior art vest of Canada patent application 590,496, (EPO Reference Number PCT International Publication #WO89/09581 dated 19 Oct. 1989), before they are doubled back to engage belt rear midsection 131 for secure fastening, as will be described.

The front midsection 132 of belt 120 presents a spaced-apart, pair of vertically oriented restraining straps 134F and 136F, which then are passed under the patient crotch and buttocks, to circle back so as to be securely attached via terminal end loops to the backside 131 of the belt, i.e., to double-looped horizontal belt mid-segment 131.

To maintain a suitable positioning athwart the patient's lower torso, at least two connecting segments 142 and 144 span the gap between the frontal and backside runs of the parallel vertical straps 134F/B and 136F/B. The rear segment of belt 120, also has upper connecting segment 131, which is flanked laterally by the permanently looped ends of vertical straps 134B, 136B. These vertical rear loops 138 and 140 (also FIG. 4) are permanently secured to either end of the horizontal mid-segment 131, and serve as the doubling back terminal for the free ends 148, 150 of belt forming straps 126 and 122, as shown better in FIG. 4.

Each of the free ends of belt forming straps are provided with the ring-like element 122, 124, respectively, which will each engage the snap-clip ends 110 of the cooperating anchoring straps 110 (FIG. 1), which were described above. Proximal to the lateral sides of opposing straps 126/128 are mounted vertically-oriented, flexible pairs of loops 152A/B, and 154A/B, respectively, through which the belt strap free longitudinal ends 148/150 are passed, before their snap-clip engagement with associated anchoring straps.

In the reverse-side view of FIG. 3, the mode of fixed rear side attachment of buttocks-encircling vertical straps (136B/134B), to the double back runs of the horizontal belt loops 124/126 is shown. Also, near the lateral sides of horizontal belt segment are vertically oriented, outer soft loops 152B and 156B, which also serve to contain the closed free ends 148/150 of belt girth straps 126/128, when a patient of large lower girth is being protected.

The elevational view of FIG. 4 is of the safety belt front side, but now depicted with the horizontal belt straps 126, 128 disengaged from their functional, Velcro-type retention. This reveals the substantial length, of the underlying pads of complemental fastening material, fixedly mounted on the inside of the horizontal belt. Preferably, the adhesive pile segment is on the inner belt portion 160B/162B, and the hook-locking segment 160F/162F, is disposed on the outer strap portion.

Both the restraining vest and cooperating safety belt of the present invention provide a marked improvement over earlier known garments. They provide for secure restraining means, which cannot be released by the restless patient, since the sliding buckles, like 112 and the snappable fastener, like 110 on anchoring strap 100, are located distally from a patient; yet, it is these components that are comparatively inexpensive to fabricate, requiring no unusual hardware. They also involves no integral component which can become hazardous to the patient.

Safety belt 120 of FIGS. 2 to 4, can be employed in conjunction with the safety vest of my U.S. Pat. No. 4,832,053 so as to provide added security with a seated patient. Firstly, left end ring 122 of the belt passes through one lower loop 25 on the vest front panel 21. Be sure that both front loops (152A/154A) on the belt pass through the lower loops on the vest. Repeat the step, threading the other belt ring 124 through the opposing front loop 26 on the vest. Again, both the belt strap free ends should slide through the vest loop. Later, when resorting to the anchoring straps (FIG. 1), one will need to couple the belt rings 122/124, with the strap rings like 28.

The dual strand, webbed material, elongate crotch strap 134F/136F should be passed between the patient's legs and doubled back to the rear panels on the safety vest. To connect this webbed section to the side belt strap, thread each belt ring, 122/124, through one loop (154B) on the terminal end of the webbed section. One one end, double back the strap 128 free end 150, matching the Velcro pad in the strap center, and then thread the end ring 124 of the belt through the dual side loops 154F/159B.

Repeat these steps for the other belt strap 126, threading, doubling back and matching the Velcro pads, finally threading end ring 122 through paired loops 152A/152B. Now, the integrated safety vest and belt are properly enclosed about the patient who has been secured, as needed, in a wheelchair, or safety chair. Safety belt 120 is not usually employed with a bed-ridden patient.

Most impressively, it handily permits necessary re-adjustments of the patient's body, without risking an injurious fall from the supporting bed, or any contortions by an agitated patient that could convert the vest edges into a strangulation ligature, as has been discussed.

In the perspective view of FIG. 5, the configuration of a special anchoring strap 160 is depicted. Each of its longitudinal planar fabric ends 162, 164 is looped through a transversely configured, rigid slotted base 166 of fastener 168. Each such slot is integral with a conventional, snap-spring fastener 170, typically one with a partial hook-shaped rigid end and a cooperating flexible metal (or plastic) snap strip 172. Snap 172 is biased to be normally closed within the inner tip 174 of hooked end 176. Snap 172 is also adapted to be digitally depressed so as to permit instant release of an ensnared ring, like floating D-ring 178.

On the elongate intermediate body of anchor strap 160, there is mounted a conventional, double-slot rigid buckle 180 which tracks along the free fabric length. In this manner, the overall strap 160 length is substantially variable, but is also presettable, so as to tightly straddle the distance between the restraint attachment point and a particular remote stationary post, typically a bed vertical post or railing. A rigid, hemispherical (D) attachment ring 178 may slide along the intermediate span of strap 160, but is usually located proximal to the fastener snap 168.

In the top plan view of FIG. 6, a safety restraint 181 is laid out to its full extension, as it would appear before its assembly for use according to the present invention. At one (upper) longitudinal end 182, the belt terminates in a planar fabric loop usually sewn transversely. The use of the end of belt loop will be described. Another such rigid ring 186 is located fixedly along the intermediate length of the belt, but is located far more proximal to the other longitudinal end thereof. Similar to anchor strap 160, a slidable, double-slotted buckle 188 is located between crotch strap 190 and upper longitudinal end 182 mounted transversely upon the belt run.

Buckle 188 is slipped upon the belt run so as to engage central fabric loop 200 freely, before the formation of planar fabric loop 204 . Buckle 188 is thus deployed to slidingly position the belt free end to be disposed adjacent a patient's stomach. The width of lateral end loop 204 precludes a patient from threading the thusly engaged belt end back through buckle 188 and then out of engagement with central loop 200. This avoids throwing off of the belt harness by a diligent patient at an inappropriate time.

Adjacent the lower longitudinal end 183 is secured an adjacent pair of complemental pile and hook-locking segments 194, 196, but located only on the one stirface of the belt end. As for the specific juxtaposition of these known Velcro™-type material fasteners, the adhesive pile component 194 may be more conveniently mounted abutting the D-ring 189, while the hook-pacts 196 is mounted, spaced apart slightly, but just inwardly thereof. These complemental segments are engaged after torso encirclement, as will be described. Either arrangement is operable but that just detailed is preferred for ease of manual manipulation.

Disposed essentially midway of the ends of the restraint belt 181 is secured a depending (upon assembly) single, fabric-strap 190. Crotch strap 190 is of a length sufficient to engage the girth of a patient's buttocks. In the depicted embodiment, near the crotch strap free end 192, it is provided with a detachable closure element 193, that permits of instant release of this encircling strap. A suitable, snap and closure and release means is such as that provided for motor vehicle seat belts, or a simple attachment and release means may be used, like means 168 on the strap of FIG. 5.

Alternatively, the free, or loose, end 192 may be looped, and sewn so as to fixedly engage large central ring 200 in a rotatable but permanent mode. Large fabric ring 200 is sewn into permanent engagement with the left-side upper longitudinal end 182 running to the back of belt 181.

The perspective view of FIG. 7 depicts the belt restraint of FIG. 6 while in use. After enclosing the lower torso 201, the right-side, longitudinal belt end 183 (lower in FIG. 5) is threaded first through central fabric ring 200, and then under outer belt loop 198, so that its adhesive pads 194, 196 (of FIG. 6) make secured contact, leaving D-ring 184 projecting outwardly, and so for attachment to other components (not seen). The opposing lateral belt segment 202 projects D-ring 186 and integral fabric loop 204, also outwardly. Laterally-located fabric loop 204 is priarily provided for sliding engagement with the modified anchor strap of FIG. 5. In this manner, the restrained patient can be loosely tethered to a remote post, while still permitting considerable freedom of the torso.

For example, after patient positioning, anchor strap 160 of FIG. 5 is threaded through the front-side soft loop 204, followed by extending the ensnared anchor strap to a remote stationary post (not seen).

LIMB RESTRAINT DEVICE

An ancillary device that can also be usefully employed by cooperating with the belt restraint just described for a chronically agitated patient, is the limb restraint (wrist) shown in FIGS. 10/13, for those patients also needing limb protection. This limb cuffing means 210 is provided with a centrally and partially padded, flexible fabric base member 211 of a generally rectangular configuration. The free ends of limb restraint 210 are interruptably mateable via a complemental pair of Velcro™-type fastening pairs 212, 214, a double ribbon-like, fastening means 216 and an integrally associated, but separable, anchoring strap 229 (FIG. 10). Such a strap may be secured to the arm (or leg) rest elements of a chair or bed (not seen), as will be seen by referring to FIGS. 5 and 6 of my earlier U.S. Pat. No. 4,832,053, on FIG. 16 hereof.

The wrist restraint embodiment of FIG. 10 is comprised essentially of a flexible but strong generally rectangular woven cloth 218. Secured centrally of one surface of cloth 218 is a padded segment 220 disposed transversely of the restraint. Padded segment 220 is typically composed of a foam-shaped, resilient elastomer. Also located at one longitudinal end 222 (upper end is depicted) is a woven fabric, endless O-ring cloth fastening means 216 (mounted on base cloth 218 diametrically in a manner such as to present opposing double loops). Circular ribbon means 216 is fastened at two diametrically opposing points (transversely of the ribbon) to the parallel linear margins (long edges of planar surface 211 adjacent one longitudinal end. As depicted, it describes a symmetrically closed loop, ribbon-like configuration in its relaxed state, which is bonded peripherally (224, 226) to the underlying padded cloth at its upper margin, along one transverse dimension (222) of the cloth 218. A detachable anchor strap 229 (like that of FIG. 5) is associated therewith.

On the opposing longitudinal end (same surface 211) of member 210 is the aforedescribed adjacent pair of complemental securing means 212/214, which serves for restraint locking, as required, to engage a limb.

In one embodiment, inner (rectangular) pad 212 can be of the adhering pile type (A) (Velcro™-form), while outer pad 214 is then of the complemental hook-locking (H)type. The opposing longitudinal end 222, as noted, carries the closed fabric loop 216, mounted transversely on the same planar surface 211 to the parallel opposing linear margins thereof.

On the opposing (reverse) planar surface 228 of restraint 210, shown in FIG. 11 (at same end as fabric loop 216), it has been adapted to carry a substantially identical configuration, adjacent pair of complemental securing segments 230 and 232. They are located transversely of the fabric cloth 218, and positioned proximal to the upper transverse border 222 of surface 228. Consistent with the nature of the reverse pad set 212/214 (FIG. 10), the inner pad 232 is of the adhesive pile type (since outer pad 214 is of the multiple hook type), so to make adhering contact. Likewise, since inner pad 212 is of the adhesive pile type, then outer pad 230 is of the multiple hook type. These complemental pads can then engage firmly, but interruptably, upon contact.

Just as conveniently, adjacent pads 212/214 can be both of the multiple hook type (H) while adjacent pads 232/230 (FIG. 11) can be of the adhering pile (A) type. This option is depicted by pads 214A and 212A of FIG. 15. Complemental set of adjacent pads 230A/232A, disposed on the reverse surface of device 274, are seen in phantom in FIG. 15.

Thusly, the complemental adhering segments of each cloth member-mounted, end pair are arrayed so that when one longitudinal end is folded about a limb, then it overlaps and faces the adjacent complemental segments of the other securing pair, so to make a secure, but interruptable, contact with securing segments of the other longitudinal end. Once a wrist (or leg) is cradled within the overlapping ends of a restraint 210, and the other end is enfolded about the wrist, the protected wrist is as depicted in FIGS. 12 and 16.

The thusly cradled wrist (FIG. 12) is then indirectly linked to anchoring strap 229, which is engaged permanently, but slidably, to one loop 216L, and then runs through the other loop 216U, with the strap elongate midsection running backward to closure and release end 234. This single run is secured at its free end about a remote stationary post 236 (FIG. 12), as is the differing anchoring strap of FIG. 5, employed with the belt restraint of FIG. 7.

The vertical end view of FIG. 13 (body-side axial orientation) shows how a limb is to be enclosed by restraint 210, with tethering strap 229 doubly secured through O-loop 216L. Note the foam-padded segment 220 is interposed between the opposing planar cloth elements and the anchoring strap, easing limb constriction upon patient stretching.

The use of a dual set of Velcro™-type end pads will provide more stability to each wrist cuff, and its associated cinching strap 229. Alternatively, an adjacent adhering pile pair can be mounted on the one cloth surface and the adjacent hooking pair mounted on the opposing cloth surface but at the other longitudinal end.

In certain of the embodiments of restraint devices disclosed herein, wherein complemental pairs of adhering segments are disposed at opposing longitudinal ends are taught, it is optional which pair are the adhesive pile segments, and which are the hook-locking segments. Conveniently, with regard to the limb restraint of FIGS. 15, both of pads 212A, 214A are of the hook-locking type, while both of pads 230A/232A are of the adhesive pile type.

To employ the wrist-cuffing device of FIGS. 10/11, first wrap a patient's wrist 234 in the flexible, open cloth surface 228 of FIG. 11, insuring physical comfort and safety.

Confirm that the complemental Velcro pads (212/214 and 230/232) do make adhering contact on the underneath side of the wrist. Next, enfold the free loop 216U about the limb-engaged padded restraint. Then take the snap-hook end 234 of strap 229 (FIG. 10), encircle the folded over cloth member and pass it through the upper loop 216U secured to outer surface 211. Attach the anchor strap free end about the bed frame, as earlier described (FIG. 12). Preadjusting of the anchoring strap length, via the sliding buckle 278 may be in order, to confirm proper strap tension or leeway for wrist motion.

A modified anchor strap 260 of FIG. 14 is seen laid out in its full extension before it is to be coupled with either one of the hemispherical loops 262A, 262B, of the limb restraint embodiment of FIG. 15. At the upper one strap longitudinal end 234 is seen a free-running snap fastener assembly 266, composed of its base slotted element 266S, which can travel as mounted on the width of fabric strap 268, and its linked outwardly projecting snap hook means 266H. Also, running-free along strap 260 is a formed plastic ring 270, adapted to couple with the snap hook means 266H of fastener assembly 266, at the proper location, as will be described.

At the other longitudinal end 272 of anchor strap 260 is seen the free fabric only end 276 of the strap, before it is entwined with one of the hemiloops (262) of limb restraint device 274. End 276 it was previously doubled back on itself and is secured, as by sewing, to the proximal segment of the same longitudinal end, thus presenting a permanently engaged, slidable, fabric end loop 276 (FIG. 15).

When the strap nonfastener end 272 is thusly used, such an end loop 262A/B is threaded, deployed and associated with restraint device 274; then it presents itself as seen in the elevational view of FIG. 15, just prior to limb envelopment. This will permit each wrist and/or leg restraint device to have its own tieless anchor strap, adapted to tether that specific limb to a chair arm rest, or chair leg, while gaining the safety advantage of containing erratic and extreme limb movements by an agitated patient. Tether strap 260 needs to be of an intermediate length sufficient to be looped about a support post. The overall length of anchor strap 260 is made purposefully variable, as is that of prior anchor strap 100 (FIG. 1), simply by including along its intermediate length, the adjustable buckle 278, which is functionally identical to the like buckle 112 of the anchor strap of FIG. 1.

The limb restraint 274 and its cooperating anchor strap 260 are shown in functional engagement with a patient wrist 280 (FIG. 16), while being remotely tethered to a fixed post 282, which is either a chair arm or bed frame side rail. Anchor strap 260 has been somewhat foreshortened via buckle 278 to provide the desired tolerable amount of limb play. As seen in FIG. 16, the restraint 274 has been wrapped about the wrist, while the fixedly entwined looped end 276 of strap 220 runs back under opposing loop 262B and thence to fixed railing 282. Quick release of the tether is effected at the railing end and threading back the anchor strap back under loop 262B to open the padded segments to effect prompt release.

The present invention has been described with reference to a presently preferred embodiment thereof. Such embodiment should not be considered a limitation of the scope of the present invention. The scope of the present invention is better ascertained by reference to the following claims.

I claim:

1. A restraint device adapted for interruptable contact with a to be restrained limb and for concurrent remote anchoring to limit exaggerated limb flexing, comprising:

(a) a flexible fabric member being of a generally rectangular configuration with first and second planar surfaces having substantially parallel, opposing linear margins defining the longitudinal dimension of each of said surfaces;

(b) a flexible cloth, ribbon-like element normally describing a closed circle when not in use, said flexible cloth being partly fastened across its length at two diametrically opposite points which are transversely disposed to the parallel opposing linear margins and located on the first surface of said fabric member along one lateral transverse dimension of said cloth, and proximal to a first longitudinal end thereof, such ribbon-like element thus presenting two substantially symmetrical, hemispherical loops adapted for interruptable, looping engagement with an elongate anchoring strap;

(c) at least one first adhering segment of a pile type mounted transversely on the first planar surface of said fabric member and being located proximal to a second longitudinal end of said fabric member which is distal from the ribbon-like element;

(d) at least one second adhering segment of a hook-locking type mounted on the second planar surface of said fabric member and being located proximal to the first longitudinal end of said fabric member;

(e) the adhering segments on the first and second longitudinal ends being aligned complementally so that when the first longitudinal end of the fabric member is folded about a patient limb, and serves to overlap the second longitudinal end thereof, then the first adhering segment on the first fabric surface will contact with the second adhering segment on the second fabric surface; and (f) a separable elongate anchoring strap which cooperates with at least one of the two hemispherical loops of said ribbon-like element by being in sliding engagement at one longitudinal end to one of the hemispherical loops, and said anchoring strap adapted for being passed through the second of said hemispherical loops, while the device is disposed in the limb restraining mode, with the other longitudinal end of said anchoring strap itself terminating in an engageable element which forms an anchor strap attachment and release means, with the strap itself being of an intermediate length sufficient for such hemispherical-loop engaged strap to also extend and be strung around a support post which is spaced apart from the limb restraint device, whereby the overall flexing movement of the restrained limb is controlled by the associated anchoring strap.

2. The limb restraint device of claim 1 in which the anchoring strap further comprises a permanent loop provided at the one longitudinal end of said strap, that is normally engaged with one of said hemispherical loops of the ribbon-like element, a ring-like closure means freely tracking the strap length along the transverse strap width, and said engageable element having a complemental manually-activated snap-hooking means disposed securely at the other strap longitudinal end, and adapted to interruptably engage the closure means.

3. The restraint device of claim 1 wherein the flexible fabric member is also provided with an integral padded segment proximal a mid-section of the member, said padded segment adapted to provide a cushioning effect upon the restraint assembly during the cinching of the anchor strap through the restraint device ribbon-like element and its concurrent tethering to a remote post.

4. The restraint device of claim 1 wherein said at least one first adhering segment comprises a pair of complemental pile segments on the first fabric surface and said at least one second adhering segment comprises a pair of hook-locking segments on the second fabric surface configured so that the pair of segments on the first surface will make adhering contact with the pair of segments on the second surface when the ends of said fabric member are overlapped.

5. The device of claim 1 wherein said at least one first adhering segment on the first fabric planar surface comprises a substantially parallel, spaced-apart pair of adhering pile segments, and further wherein the said at least one second adhering segments on the second fabric planar surface comprises a substantially parallel, spaced-apart pair of complemental hook-locking segments, which will make interruptable contact with the pile segments on the obverse side when one longitudinal end of the fabric is disposed to overlap the other longitudinal end.

* * * * *